US008680262B2

(12) United States Patent
Lange et al.

(10) Patent No.: US 8,680,262 B2
(45) Date of Patent: Mar. 25, 2014

(54) PURIFICATION OF OLIGONUCLEOTIDES

(75) Inventors: Meinhof Lange, Starzach-Felldorf (DE); Olaf Groessel, Halle/Westfalen (DE); Fritz Link, Bensberg (DE); Andreas Schoenberger, Mueden/Aller (DE); Andreas Hohlfeld, Halle/Westfalen (DE)

(73) Assignee: Girindus AG (DE)

( * ) Notice: Subject to any disclaimer, the term of this patent is extended or adjusted under 35 U.S.C. 154(b) by 0 days.

(21) Appl. No.: 13/421,273

(22) Filed: Mar. 15, 2012

(65) Prior Publication Data
US 2013/0066061 A1 Mar. 14, 2013

Related U.S. Application Data

(63) Continuation of application No. 12/568,229, filed on Sep. 28, 2009, now abandoned, which is a continuation of application No. 12/402,128, filed on Mar. 11, 2009, now abandoned, which is a continuation of application No. 12/196,605, filed on Aug. 22, 2008, now abandoned, which is a continuation of application No. 11/814,429, filed as application No. PCT/EP2006/050503 on Jan. 30, 2006, now abandoned.

(60) Provisional application No. 60/647,457, filed on Jan. 28, 2005.

(30) Foreign Application Priority Data

Jan. 28, 2005 (EP) .................................... 05001768

(51) Int. Cl.
*C07H 21/00* (2006.01)
(52) U.S. Cl.
USPC ..................... 536/25.41; 536/25.4; 536/25.42
(58) Field of Classification Search
None
See application file for complete search history.

(56) References Cited

U.S. PATENT DOCUMENTS

| 5,571,902 A | 11/1996 | Ravikumar et al. |
| 6,586,586 B1 * | 7/2003 | Krotz et al. ................... 536/25.4 |
| 2003/0055241 A1 | 3/2003 | Moore et al. |

FOREIGN PATENT DOCUMENTS

| EP | 0512768 A1 | 11/1992 |
| JP | 2002293791 | 10/2002 |
| WO | WO-2004/011474 A1 | 2/2004 |

OTHER PUBLICATIONS

Thoma Methods in Enzymology (1996), vol. 274, pp. 197-214.*

* cited by examiner

*Primary Examiner* — Patrick Lewis
(74) *Attorney, Agent, or Firm* — Novak Druce Connolly Bove + Quigg LLP

(57) ABSTRACT

A method for purifying a protected oligonucleotide comprising the steps of:
a) providing a solution of the protected oligonucleotide in at least one solvent A having a boiling point below the boiling point of a solvent B,
heating the solution at a temperature of at least 30° C. and below the boiling point of the at least solvent A,
adding solvent B until precipitation of a material is visible in the solution, said solvent B being an alcohol having 1 to 6 C-atoms or a diol having 2 to 6 C-atoms,
allowing the solution to cool down under stirring until formation of a supernatant and a residue,
removing the supernatant
or
b) providing solvent B, said solvent B being an alcohol having 1 to 6 C-atoms or a diol having 2 to 6 C-atoms,
heating solvent B at a temperature above 30° C. and below the boiling point of solvent B,
adding a solution of a protected oligonucleotide in at least one solvent A until precipitation of a material is visible in the solution,
allowing the solution to cool down under stirring until formation of a supernatant and a residue,
removing the supernatant.

21 Claims, No Drawings

PURIFICATION OF OLIGONUCLEOTIDES

The present invention relates to a method for purifying oligonucleotides.

The synthesis of oligonucleotides has been the subject of intensive research for a long period of time. Automated synthesis procedures have been developed and apparatus for the automated synthesis are commercially available. Most of these procedures have been developed for rather small quantities of oligonucleotides (in the range of mg). These amounts are sufficient for most research purposes.

Especially with the development of antisense therapeutics, large scale synthesis became a matter of considerable importance. Although relative large scale synthesis procedures have been developed, one major drawback is the purification of the intermediates and products. For small scale synthesis reversed-phase HPLC is an appropriate method allowing the purification of mg quantities in short time with good purification results. For large scale production reversed-phase HPLC becomes a difficult procedure requiring large amounts of solvents, expensive apparatus and the like.

There is an ongoing need for improved methods for purifying the products of oligonucleotide synthesis.

US 2003/0055241 discloses a method for preparing purified oligonucleotides comprising treating a solution of oligonucleotide with an aggregating agent and a precipitation enhancer. The method is used for the purification of unprotected oligonucleotides or 5' protected oligonucleotides. An ionic form is needed for the precipitation enhancer to interact with the molecule.

EP 0 512 768 A1 discloses a method for purifying DNA. The DNA is prepared from natural sources.

Both methods described above can only be used for unprotected or nearly completely unprotected oligonucleotides. During synthesis, oligonucleotides are protected, therefore, the methods of US 2003/0055241 and EP 0 512 768 A1 are not applicable.

It is an object of the present invention to overcome the drawbacks of prior art and provide an efficient purification method for oligonucleotides and intermediates, especially for large scale synthesis.

In one embodiment, the present invention provides a method for purifying a protected oligonucleotide comprising the step of
  providing a solution of the protected oligonucleotide in at least one solvent A having a boiling point below the boiling point of a solvent B,
  heating the solution at a temperature of at least 30° C. and below the boiling point of the at least solvent A,
  adding solvent B until the solution becomes cloudy, said solvent B being an alcohol having 1 to 6 C-atoms or a diol having 2 to 6 C-atoms,
  allowing the solution to cool down under stirring until formation of a supernatant and a residue,
  removing the supernatant.

In a further embodiment, the invention provides a method for purifying a protected oligonucleotide comprising the steps of
  providing solvent B, said solvent B being an alcohol having 1 to 6 C-atoms or a diol having 2 to 6 C-atoms,
  heating solvent B at a temperature above 30° C. and below the boiling point of solvent B,
  adding a solution of a protected oligonucleotide in at least one solvent A until the solution becomes cloudy,
  allowing the solution to cool down under stirring until formation of a supernatant and a residue,
  removing the supernatant.

"Becomes cloudy" is an observation describing that the solution is saturated, e.g. unable to dissolve the protected oligonucleotide. A solution is cloudy if precipitation of a material is visible.

"Cooled down" means to reduce the temperature of the solution. Typically cooling down is effected to reach room temperature (about 25° C.). In some cases, it is preferred to cool further, i.e. to reach at least 20° C. or at least 10° C. or 0° C.

A "protected oligonucleotide" is an oligonucleotide comprising one or more protective groups for example at the 5', 3', 2' position of the sugar moiety and/or at the heterocyclic bases and/or at the P-linkage (e.g. phosphate or thiophosphates).

The term "protective groups" includes groups which are not removed prior to use of the oligonucleotides, e.g. modifications used to increase stability of the oligonucleotide.

A suitable protection for the 2'-hydroxyl-group include but are not limited to tert-butyl dimethylsilyl (TBDMS), triisopropylsilyloxymethyl (TOM), fluorophenylmetoxypiperidinyl (FPMP), and $CH_2$—O-Et, and non-cleavable modifications like 2'F or 2'MeO Suitable protecting groups for the 3'-hydroxyl-group include but are not limited to tert-butyl dimethylsilyl (TBDMS), levulinyl, benzoyl.

Suitable modifications include LNA (2'O-4'C-methylene bridge).

Suitable protected nucleobases are known to persons skilled in the art for example N-4-benzoylcytosine, N-6-benzoyl adenine, N-2-isobutyryl guanine, N-4-acetyl or isobutyryl cytosine, N-6-phenoxyacetyl adenine, N-2-tert-butyl phenoxyacetyl guanine. Suitable non-base residues include also hydrogen (H) leading to the 1',2'-dideoxyribose (dSpacer from Glen Research) which can be used as linker or to mimic a basic sites in an oligonucleotide (Takeshita et al., J. Biol. Chem., 1987, 262, 10171).

Suitable 5'-protection group include, but are not limited to trityl groups, preferably a dimethoxytrityl group (DMTr) or a monomethoxytrityl group (MMTr). These protection groups are used in conventional prior art solid phase oligonucleotides synthesis. Other suitable 5'-protection groups include, but are not limited to tert-butyl dimethylsilyl (TBDMS), levulinyl, benzoyl, fluorenemethoxycarbonyl (FMOC), 9-phenylthioxanthen-9-yl (S-pixyl).

In a preferred embodiment, the protected oligonucleotide is a non-ionic compound.

An "oligonucleotide" is an oligomer of monomeric units comprising sugar units connected to heterocyclic bases, said monomeric units being connected via linkages. Typical linkages are derivatives of phosphor, for example phosphates, thiophosphates or derivatives thereof. The term also covers oligonucleosides, oligonucleotide analogs, modified oligonucleotides, nucleotide mimetics and the like in the form of RNA and DNA. In general, these compounds comprise a backbone of linked monomeric subunits where each linked monomeric subunit is directly or indirectly attached to a heterocyclic base moiety. The linkages joining the monomeric sub-units, the monomeric subunits and the heterocyclic base moieties can be variable in structure giving rise to a plurality of motives for the resulting compounds.

According to preferred embodiments of the invention, the protected oligonucleotide has a length of 2 to 30 nucleotides, preferably 2 to 9, preferably 2 to 6.

Modifications known in the art are the modification of the heterocyclic bases, the sugar or the linkages joining the monomeric subunits. Variations of internucleotide linkages are for example described in WO 2004/011474, starting at the bottom of page 11, incorporated by reference.

Typical derivatives are phosphorthioates, phosphorodithioates, methyl and alkyl phosphonates and phosphonoaceto derivatives.

Further typical modifications are at the sugar moiety. Either the ribose is substituted by a different sugar or one or more of the positions are substituted with other groups such as F, O-alkyl, S-alkyl, N-alkyl. Preferred embodiments are 2'-methyl and 2'-methoxyethoxy. All these modifications are known in the art.

Concerning the heterocyclic base moiety, there are a number of other synthetic bases which are used in the art, for example 5-methyl-cytosine, 5-hydroxy-methyl-cytosine, xanthin, hypoxanthin, 2-aminoadenine, 6- or 2-alkyl derivatives of adenine and guanine, 2-thiouracyl. Such modifications are also disclosed in WO 2004/011474 starting from page 21.

The protected oligonucleotide may have a 5' and 3' protection group or a 5' protection group and no 3' protection group or a 3' protection group and no 5' protection group. It may—depending on the structure of the oligonucleotide—have a 2' protection group.

Is preferred, that the P-linkage and the heterocyclic bases will be suitably protected.

In one embodiment, the protected oligonucleotide is dissolved in a solvent or a mixture of solvents wherein one of the solvents is designated as solvent A. Suitable solvents A are for example $CH_2Cl_2$, $CHCl_3$, tetrahydrofuran, acetonitril, methanol, ethanol, dichlorethane, tetrachlorethane, dioxane, acetone.

While one solvent might be sufficient for some protected oligonucleotides in another embodiment it is preferred to use a mixture of solvents for example selected from $CH_2Cl_2$, $CHCl_3$, tetrahydrofuran, acetonitrile, methanol, ethanol, dichlorethane, tetrachlorethane, dioxane, acetone.

According to the invention, the solution of the protected oligonucleotide is heated at a temperature of at least 30° C. but below the boiling point of the at least one solvent A. If a mixture of solvents is used for the solution of the protected oligonucleotide it is preferred that the solution is not heated above the boiling point of any ingredient of the mixture.

Thereafter, a solvent B, an alcohol or diol is added to the solution.

It is preferred that solvent A has a boiling point below the boiling point of solvent B but good results can also be achieved with solvents A and B having a similar boiling point or even situations wherein the boiling point of solvent A is higher than the boiling point of solvent B.

A very preferred solvent A comprises $CH_2Cl_2$ (preferably at least 90% by weight) and a very preferred solvent B comprises isopropanol (preferably at least 90% by weight). A combination of $CH_2Cl_2$ and isopropanol is especially useful and, therefore, preferred.

A further embodiment of the invention is a method comprising
  providing a solution of a protected, non-ionic oligonucleotide in at least one solvent A,
  combining said solution with solvent B to form a solvent A+B wherein the amounts of solvent A and solvent B are selected to have a saturated solution of the non-ionic, protected oligonucleotide in solvent A+B,
  and waiting until formation of a supernatant and a residue.
This solvent B is an alcohol having 1 to 6 C-atoms or a diol having 2 to 6 C-atoms.

Unless the necessary amount is exactly known, it is preferred to add solvent B drop wise. Upon addition of solvent B the solution becomes cloudy but in most cases, the solution becomes clear again upon further stirring and/or heating. As the boiling point of solvent B is higher than the boiling of solvent A, the temperature of the solution increases upon further heating. The preferred amount of solvent B is the amount which has to be added to have the solution stay cloudy or a little bit less of solvent B.

In one embodiment, the solution is heated at a temperature in the range of 5 to 10° C. below the boiling point. Once the solution is cloudy, it is heated at the boiling point for one minute and then allowed to cool down.

Heating of the solution is especially preferred if the impurities are large, i.e. the purity of the oligonucleotide is below 85%. In this case, the heating increases the purification efficiency. If purity is higher (i.e. about at least 90%) or a reduced purification efficiency is acceptable, the method of the present invention can also be effected at a temperature of about 25 to 30° C. or even at a temperature between 15 and 25° C. Purification is less efficient at lower temperatures.

In some embodiments, it is useful to repeat the method of the present invention. In these cases the first purification step could be effected at a temperature of at least 30° C. and subsequent purification steps at a lower temperature, i.e. 20° C. or 25° C. Thereafter, the solution is allowed to cool down under stirring. Cooling can be effected to room temperature or even to lower temperatures for example with a refrigerator.

It is preferred to stir these solutions during cooling. In a preferred embodiment stirring is continued for at least three hours, preferably six hours and most preferred overnight.

According to the method of the invention, a supernatant and a residue are formed. The supernatant comprises impurities and is removed and discarded. The residue can be of different forms, it can be a gel, an oil or it can be in a crystalline form. In some embodiments, it is helpful to add an ether to the residue and remove the ether again together with further impurities. The protected oligonucleotide is not soluble in the ether.

In some cases, this treatment with ether increases the tendency to form crystalline or powder forms of the residue.

In a preferred embodiment, the purification treatment is repeated at least once. A solvent or solvent mixture of the solvent type A is added and the oligonucleotide is redissolved. Thereafter, the purification method of the present invention is repeated.

The method of the present invention is especially suitable for larger scale synthesis, i.e. starting from about 100 mg quantities to quantities of kg. The equipment needed for the method of the present invention are cheap compared to a large scale HPLC.

The method of the present invention is especially useful to remove catalysts such as tetrazole, DCI or BMT and sulfurizing agents such as PADS.

The invention is further explained with reference to the following non-limiting examples:

1) 5'-O-DMTr-$C^{Bz}$-P(S, OCNE)-$C^{Bz}$-3'-O-Lev (10.8 mmol)

were dissolved in 25 ml dichloromethane and heated to 40° C. Addition of 120 ml 2-propanol (1:4.8) while the solution was heated until 55-60° C. After the addition of 2-propanol the mixture was cooled to room temperature and stirred overnight. The purified product was isolated as a colourless residue. The purity increased from 77.2 to 88.0% after one purification. By using 5'-O-TBDMS-$C^{Bz}$-P(S, OCNE)-$C^{Bz}$-3'-O-Lev the purity increased from 78.1% to 94.8% after 2 purifications.

2) 5'-O-DMTr-$A^{Bz}$-P(S, OCNE)-$G^{iBu}$-3'-O-Lev (15 mmol)

were dissolved in 50 ml dichloromethane and heated to 40° C. Addition of 450 ml 2-propanol (1:9) while the solution was heated until 50-55° C. After the addition of 2-propanol the mixture was cooled to room temperature and stirred over night. The purified product was isolated as a colourless residue. The purity increased from 50.8 to 79.5% after 2 purifications.

3) 5'-O-DMTr-$A^{Bz}$-P(S, OCNE)-$G^{iBu}$-3'-OH (1.63 mmol)

were dissolved in 20 ml dichloromethane and heated to 40° C. Addition of 400 ml 2-propanol (1:20) while the solution was heated until 50-55° C. After the addition of 2-propanol the mixture was cooled to room temperature and stirred over night. The purified product was isolated as a colourless residue. The purity increased from 79.5 to 93.2% after 2 purifications.

4) 5'-O-DMTr-$C^{Bz}$-P(S, OCNE)-$G^{iBu}$-3'-O-Lev (7.58 mmol)

were dissolved in 12 ml dichloromethane and heated to 40° C. Addition of 130 ml 2-propanol (1:10.8) while the solution was heated until 50-55° C. After the addition of 2-propanol the mixture was cooled to room temperature and stirred over night. The purified product was isolated as a colourless residue. The purity increased from 62.5 to 88.7% after 2 purifications.

5) 5'-O-DMTr-$C^{Bz}$-P(S, OCNE)-$G^{iBu}$-3'-OH (2.0 mmol)

were dissolved in 10 ml dichloromethane and heated to 40° C. Addition of 70 ml 2-propanol (1:4.8) while the solution was heated until 50-55° C. After the addition of 2-propanol the mixture was cooled to room temperature and stirred over night. The purified product was isolated as a colourless residue. The purity increased from 88.2 to 95.5% after 2 purifications.

6) 5'-O-DMTr-T-P(S, OCNE)-$G^{iBu}$-3'-O-Lev (10.2 mmol)

were dissolved in 30 ml dichloromethane and heated to 40° C. Addition of 450 ml 2-propanol (1:15) while the solution was heated until 50-55° C. After the addition of 2-propanol the mixture was cooled to room temperature and stirred over night. The purified product was isolated as a colourless residue. The purity increased from 68.0 to 96.2% after one purification.

7) 5'-O-DMTr-T-P(S, OCNE)-$C^{Bz}$-P(S, OCNE)-$C^{Bz}$-P(S, OCNE)-$C^{Bz}$-3'-O-Lev (1.41 mmol)

were dissolved in 15 ml dichloromethane and heated to 40° C. Addition of 50 ml 2-propanol (1:3,3) while the solution was heated until 50-55° C. After the addition of 2-propanol the mixture was cooled to room temperature and stirred over night. The purified product was isolated as a colourless residue. The purity increased from 68.0 to 89.6% after 2 purifications, 8) 5'-O-H-T-P(S, OCNE)-$C^{Bz}$-P(S, OCNE)-$C^{Bz}$-P(S, OCNE)-$C^{Bz}$-3'-O-Lev (0.33 mmol)

were dissolved in 5 ml dichloromethane and heated to 40° C. Addition of 11 ml 2-propanol (1:2.2) while the solution is heated until 50-55° C. After the addition of 2-propanol the mixture was cooled to room temperature and stirred over night. The purified product was isolated as a colourless residue. The purity increased from 59.2 to 83.7% after two purifications.

9) 5'-O-DMTr-T-P(S, OCNE)-$C^{Bz}$-P(S, OCNE)-T-P(S, OCNE)-$C^{Bz}$-P(S, OCNE)-$C^{Bz}$-P(S, OCNE)-$C^{Bz}$-3'-O-Lev (0.26 mmol)

were dissolved in 5 ml dichloromethane and heated to 40° C. Addition of 11 ml 2-propanol (1:2.2) while the solution is heated until 50-55° C. After the addition of 2-propanol the mixture was cooled to room temperature and stirred over night. The purified product was isolated as a colourless residue. The purity increased from 57.6 to 94.3% after three purifications.

10) 5'-O-DMTr-T-P(S, OCNE)-$C^{Bz}$-P(S, OCNE)-T-P(S, OCNE)-$C^{Bz}$-P(S, OCNE)-$C^{Bz}$-P(S, OCNE)-$C^{Bz}$-3'-OH (0.22 mmol)

were dissolved in 10 ml dichloromethane and heated to 40° C. Addition of 30 ml 2-propanol (1:3) while the solution is heated until 50-55° C. After the addition of 2-propanol the mixture was cooled to room temperature and stirred over night. The purified product was isolated as a colourless residue. The purity increased from 90.1 to 95.2% after one purification.

11) 5'-O-DMTr-$C^{Bz}$-P(S, OCNE)-$G^{iBu}$-P(S, OCNE)-T-P(S, OCNE)-$G^{iBu}$-3'-O-Lev (0.74 mmol)

were dissolved in 10 ml dichloromethane and heated to 40° C. Addition of 60 ml 2-propanol (1:6) while the solution is heated until 55-60° C. After the addition of 2-propanol the mixture was cooled to room temperature and stirred over night. The purified product was isolated as a colourless residue. The purity increased from 47. 6 to 80.6% after two purifications.

12) 5'-OH-$C^{Bz}$-P(S, OCNE)-$G^{iBu}$-P(S, OCNE)-T-P(S, OCNE)-$G^{iBu}$-3'-O-Lev (0.23 mmol)

were dissolved in 20 ml dichloromethane and heated to 40° C. Addition of 100 ml 2-propanol (1:5) while the solution is heated until 55-60° C. After the addition of 2-propanol the mixture was cooled to room temperature and stirred over night. The purified product was isolated as a colourless residue. The purity increased from 70.2 to 85.2% after two purifications.

13) 5'-O-DMTr-$A^{Bz}$-P(S, OCNE)-$G^{iBu}$-P(S, OCNE)-$C^{Bz}$-P(S, OCNE)-$G^{iBu}$-P(S, OCNE)-T-P(S, OCNE)-$G^{iBu}$-3'-O-Lev (0.2 mmol)

were dissolved in 10 ml dichloromethane and heated to 40° C. Addition of 45 ml 2-propanol (1:4.5) while the solution is heated until 50-55° C. After the addition of 2-propanol the mixture was cooled to room temperature and stirred over night. The purified product was isolated as a colourless residue. The purity increased from 45.2 to 77.9% after two purifications.

14) 5'-O-DMTr-A$^{Bz}$-P(S, OCNE)-G$^{iBu}$-P(S, OCNE)-C$^{Bz}$-P(S, OCNE)-G$^{iBu}$-P(S, OCNE)-T-P(S, OCNE)-G$^{iBu}$-3'-OH (0.1 mmol)

were dissolved in 5 ml dichloromethane and heated to 40° C. Addition of 8 ml 2-propanol (1:1.6) while the solution is heated until 50-55° C. After the addition of 2-propanol the mixture was cooled to room temperature and stirred over night. The purified product was isolated as a colourless residue. The purity increased from to 72.2% 88.4 after three purifications.

15) 5'-OH-C$^{Bz}$-P(S, OCNE)-C$^{Bz}$-P(S, OCNE)-A$^{Bz}$-P(S, OCNE)-T-3'-O-Lev (0.72 mmol)

were dissolved in 25 ml dichloromethane and heated to 40° C. Addition of 120 ml 2-propanol (1:4.8) while the solution is heated until 55-60° C. After the addition of 2-propanol the mixture was cooled to room temperature and stirred over night. The purified product was isolated as a colourless residue. The purity increased from 75.3 to 92.1% after two purifications.

16) 5'-O-H-C$^{Bz}$-P(S, OCNE)-G$^{iBu}$-P(S, OCNE)-C$^{Bz}$-P(S, OCNE)-C$^{Bz}$-P(S, OCNE)-A$^{Bz}$-P(S, OCNE)-T-3'-O-Lev (0.69 mmol)

were dissolved in 100 ml dichloromethane and heated to 40° C. Addition of 300 ml 2-propanol (1:3) while the solution is heated until 55-60° C. After the addition of 2-propanol the mixture was cooled to room temperature and stirred over night. The purified product was isolated as a colourless residue. The purity increased from 55.3 to 95.3% after three purifications.

17) 5'-O-DMTr-C$^{Bz}$-P(S, OCNE)-A$^{Bz}$-P(S, OCNE)-T-3'-O-Lev (6.0 mmol)

were dissolved in 25 ml dichloromethane and 1 ml Methanol and heated to 40° C. Addition of 120 ml 2-propanol (1:4.8) while the solution is heated until 50-55° C. After the addition of 2-propanol the mixture was cooled to room temperature and stirred over night. The purified product was isolated as a colourless residue. The purity increased from 66.2 to 91.8% after two purifications.

18) 5'-O-DMTr-T-P(O, OCNE)-C$^{Bz}$-3'-OH (15.1 mmol)

were dissolved in 50 ml dichloromethane at 20°. Addition of 700 ml 2-propanol (1:14) while the solution was stirred at 30°. After the addition of 2-propanol the mixture was stirred and cooled to room temperature over night. The purified product was isolated as a colorless residue. Purity increased from 79.2% to 91.3% after two purification.

19) 5'-O-DMTr-G$^{iBu}$-P(O, OCNE)-T-P(O, OCNE)-T-P(O, OCNE)-G$^{iBu}$-3'-O-Lev (0.76 mmol)

were dissolved in 10 ml dichloromethane and 1 ml methanol at 20°. Addition of 30 ml 2-propanol (1:3) while the solution was stirred at 30°. After the addition of 2-propanol the mixture stirred and cooled to room temperature over night. The purified product was isolated as a colorless residue. Purity increased from 79.2% to 91.3% after one purification.

20) 5'-O-DMTr-T-P(O, OCNE)-C$^{Bz}$-P(O, OCNE)-G$^{iBu}$-P(O, OCNE)-T-P(O, OCNE)-T-P(O, OCNE)-G$^{iBu}$-3'-O-Lev (0.38 mmol)

were dissolved in 10 ml dichloromethane and 1 ml methanol at 20°. Addition of 50 ml 2-propanol (1:5) while the solution was stirred at 30°. After the addition of 2-propanol the mixture stirred and cooled to room temperature over night. The purified product was isolated as a colorless residue. Purity increased from 50.8% to 70.3% after one purification.

The invention claimed is:

1. A method for purifying a protected oligonucleotide comprising:
   a1) providing a solution of said protected oligonucleotide in at least one solvent (A) having a boiling point below the boiling point of a solvent (B);
   a2) heating said solution of said protected oligonucleotide in at least one solvent (A) at a temperature of at least 30° C. and below the boiling point of said at least one solvent (A);
   a3) adding solvent (B) to said solution until precipitation of a material is visible, said solvent (B) being an alcohol having 1 to 6 carbon atoms or a diol having 2 to 6 carbon atoms;
   a4) allowing said solution to cool down under stirring until formation of a supernatant and a residue; and
   a5) removing said supernatant; or
   b1) providing solvent (B), said solvent (B) being an alcohol having 1 to 6 carbon atoms or a diol having 2 to 6 carbon atoms;
   b2) heating said solvent (B) at a temperature above 30° C. and below the boiling point of said solvent (B);
   b3) adding a solution of a protected oligonucleotide in at least one solvent (A) to said solvent (B) until precipitation of a material is visible in the solution;
   b4) allowing said solution to cool down under stirring until formation of a supernatant and a residue; and
   b5) removing said supernatant.

2. The method of claim 1, wherein said protected oligonucleotide comprises from 2 to 30 nucleotides.

3. The method of claim 1, wherein said protected oligonucleotide comprises a 3' and 5' protection group, a 5' protection group and no 3' protection group, or a 3' protection group and no 5' protection group.

4. The method of claim 3, wherein said 5' protection group is DMTr, MMTr, tert-butyl dimethylsilyl, levulinyl, benzoyl, fluorenemethoxycarbonyl, or 9-phenylthioxanthen-9-yl.

5. The method of claim 1, wherein said solvent A is $CH_2Cl_2$, $CHCl_3$, tetrahydrofuran, acetonitrile, methanol, ethanol, dichloroethane, tetrachloroethane, dioxane, or acetone.

6. The method of claim 1, wherein said solution of a protected oligonucleotide in at least one solvent (A) comprises a mixture of solvents selected from the group consisting of $CH_2Cl_2$, $CHCl_3$, tetrahydrofuran, acetonitrile, methanol, ethanol, dichloroethane, tetrachloroethane, dioxane, and acetone.

7. The method of claim 1, wherein said solution of a protected oligonucleotide in at least one solvent (A) in a2) and said solvent B in b2) is heated at a temperature between 40 and 70° C.

8. The method of claim 1, wherein said solvent (B) is added drop wise in a3).

9. The method of claim 1, wherein the ratio between the volume of said solution of a protected oligonucleotide in at least one solvent (A) and the volume of said solvent (B) is from 1:1 to 1:100.

10. The method of claim 9, wherein said ratio is from 1:1 to 1:10.

11. The method of claim 1, wherein said residue is a gel, an oil, or crystalline.

12. The method of claim 1, further comprising adding an ether to said residue and then removing said ether together with impurities.

13. The method of claim 1, further comprising dissolving said residue to form a solution comprising at least one solvent (A) and repeating a1) through a5) or b1) through b5) at least once.

14. The method of claim 1, wherein
   a) said solvent (B) is added in a3) until precipitation of a material is visible in the solution even upon further heating; or
   b) said solution of a protected oligonucleotide in at least one solvent (A) is added in b3) until precipitation of a material is visible in the solution even upon further heating.

15. The method of claim 1, wherein said solvent (B) is selected from the group consisting of methanol; ethanol; 1,2-dihydroxyethane; 1-propanol; 2-propanol; butanol; and pentanol.

16. The method of claim 1 wherein said solvent (A) is $CH_2Cl_2$ and said solvent (B) is 2-propanol.

17. A method for purifying a protected, non-ionic oligonucleotide comprising
   a) providing a solution of said protected, non-ionic oligonucleotide in at least one solvent (A);
   b) combining said solution with a solvent (B) to form a solvent (A+B), said solvent B being an alcohol having 1 to 6 carbon atoms or a diol having 2 to 6 carbon atoms,
   wherein said protected, non-ionic oligonucleotide is more soluble (weight/volume) at 25° C. in said solvent (A) than in said solvent (B), and
   wherein the amounts of said solvent (A) and said solvent (B) are selected to have a saturated solution of said protected, non-ionic oligonucleotide in said solvent (A+B);
   c) waiting until formation of a supernatant and a residue; and
   d) removing said supernatant.

18. The method of claim 17, wherein said solvent (A) is $CH_2CH_2$, $CHCl_3$, tetrahydrofuran, or dioxane.

19. The method of claim 17, wherein said solvent (B) is isopropanol, 1-propanol, or ethanol.

20. The method of claim 17, wherein said solution (A+B) is cooled down at least 10° C. to enhance formation of said supernatant and residue.

21. The method of claim 1, wherein said protected oligonucleotide comprises from 2 to 6 nucleotides.

* * * * *